US006277855B1

(12) United States Patent
Yerxa

(10) Patent No.: US 6,277,855 B1
(45) Date of Patent: Aug. 21, 2001

(54) METHOD OF TREATING DRY EYE DISEASE WITH NICOTINIC ACETYLCHOLINE RECEPTOR AGONISTS

(75) Inventor: Benjamin R. Yerxa, Raleigh, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 09/557,059

(22) Filed: Apr. 21, 2000

(51) Int. Cl.[7] .......................... A61K 31/505; A61K 31/44

(52) U.S. Cl. .......................... 514/256; 514/299; 514/912

(58) Field of Search ..................................... 514/256, 299, 514/912

(56) References Cited

U.S. PATENT DOCUMENTS

| | | | |
|---|---|---|---|
| 4,753,945 | 6/1988 | Gilbard et al. | 514/263 |
| 4,868,154 | 9/1989 | Gilbard et al. | 514/13 |
| 5,696,166 | * 12/1997 | Yanni et al. | 514/573 |
| 5,723,477 | 3/1998 | McDonald et al. | 514/340 |
| 5,741,802 | 4/1998 | Kem et al. | 514/334 |
| 5,817,679 | 10/1998 | Shen et al. | 514/339 |
| 5,830,904 | 11/1998 | Crooks et al. | 514/317 |
| 5,861,423 | 1/1999 | Caldwell et al. | 514/351 |
| 5,900,407 | 5/1999 | Yerxa et al. | 514/47 |
| 5,922,723 | 7/1999 | Bencherif et al. | 514/256 |

FOREIGN PATENT DOCUMENTS

WO 97/46554   12/1997   (WO).
WO 98/34593   8/1998   (WO).

OTHER PUBLICATIONS

Badio, et al., "Synthesis and nicotinic activity of epiboxidine: an isoxazole analogue of epibatidine,"—*Eur. J. Pharmacol.* 321:189–194 (1997).
Baldridge, W., "Optical Recordings of the Effects of Cholinergic Ligands on Neurons in the Ganglion Cell Layer of Mammalian Retine,"—*J. Neuroscience.* 16:5060–5072 (1996).
Benowitz, N and Peyton Jacob III., "Pharmacokinetics and Metabolism of Nicotine and Related Alkaloids,"—*Neuronal Nicotinic Receptors: Pharmacology and Therapeutic Opportunities*, p.213–234 (1999).
Brioni, J. and Stephen P. Arneric., "Nicotinic Receptor Agionists Facilitate Retention of Avoidence Training: Participation of Dopaminergic Mechanisms,"—*Behav. Neural. Biol.* 59:57–62 (1996).
Brioni, J., et al., "The Pharmacology of (–)–Nicotine and Novel Cholinergic Channell Modulators,"—*Adv. Pharmacol.* 37:153–214 (1997).
Carstens, E., et al., "Activation of Neurons in Rat Trigeminal Subnucleus Caudalis by Different Irritant Chemicals Applied to Oral or Ocular Mucosa,"—*J. Neurophysiol.,* 80:465–492 (1998).

Coles, S., et al., "Hypersecrtion of Mucus Glycoproteins in Rat Airways Induced by Tobacco Smoke,"—*Am. J. Pathology* 94:459–471 (1979).
Dartt, D., p. 1–9, in Lacrimal Gland, Tear Film and Dry Eye Syndromes, Ed. Sullivan, Plenum Press, New York, (1994).
Finnie, I., et al., "Stimulation of colonic mucin synthesis by corticosteroids and nicotine,"—*Clin. Sci.,* 91:359–364 (1996).
Forstner, G., et al., "Clinical Aspects of Gastrointestinal Mucus,"—*Adv. Exp. Med. Biol.* 144:199–224 (1982).
Garvey, D., et al., "Ligans for Brain Cholinergic Channel Receptors: Synthesis and in Vitro Characterization of Novel Isoxazoles and Isothiazoles as Bioisosteric Replacements for the Pyridine Ring in Nicotine,"—*J. Med. Chem.,* 37:4455–4463 (1994).
Gilbard, J., et al., "Treatment of Keratoconjunctivitis Sicca in Rabbits with 3–Isobutyl–1–Methylxanthine,"—*Inv. Opthal. Vis. Sci.* 112:1614–1616 (1994).
Gilbard, J., "Dry Eye: Pharmacological Approaches, Effects, and Progress,"—*CLAO Jour.,* 22(2):141–145 (1996).
Gilbard, J., et al., "Stimulation of Tear Secretion and Treatment of Dry–Eye Disease with 3–Isobutyl–1–methylxanthine,"—*Arch Ophthal,* 109:672–676 (1991).
Gilbard, J., et al., "Stimulation of Tear Secretion by Topical Agents that Increase Cyclic Nucleotide Levels,"—*Inv. Opthal. Vis. Sci.* 31:1381–1388 (1990).
Holladay, M., et al., "Natural Products as a Source of Nicotinic Acetylcholine Receptor Modulators and Leads for Drug Discovery,"—Neuronal Nicotinic Receptors, Eds. Arneric and Brioni, Weley–Liss, Inc. p.253–270 (1999).
Hummer, B., et al., "Stimulation of Submucosal Glands by Nocotine Applied Locally to the Airway Mucosa,"—*Klin. Wochenschr.* 66:161–169 (1988).
Jensen, et al., Poster Presentation at American Academy of Optometry Annual Meeting, Dec. 1999, Seattle, WA.

(List continued on next page.)

*Primary Examiner*—Zohreh Fay
(74) *Attorney, Agent, or Firm*—Alberta P. Halluin; Viola T. Kung; Howrey Simon Arnold & White, LLP

(57) ABSTRACT

The invention provides a method for increasing hydration and lubrication of lacrimal tissues in a subject in need of such treatment. The method comprises administering to the subject a nicotinic acetylcholine receptor agonist such as nicotine and its analogs, transmetanicotine and its analogs, epibatidine and it analogs, lobeline and its analogs, pyridol derivatives, para-alkylthiophenol derivatives, and imidacloprid and its analogs, in an amount effective to stimulate mucus secretion in the lacrimal system. Pharmaceutical formulations and methods of making the same are also disclosed. Methods of administering the formulation include: topical administration via a liquid, gel, cream, or as part of a contact lens or selective release membrane; or systemic administration via nasal drops or spray, inhalation by nebulizer or other device, oral form (liquid or pill), injectable, intra-operative instillation, suppository form, or transdermal form. The invention is useful for treating dry eye disease and corneal injury.

21 Claims, No Drawings

OTHER PUBLICATIONS

Jumblatt, J., et al., "Regulation of Ocular Mucin Secretion by P2Y2 Nucleotide Receptors in Rabbit and Human Conjunctiva,"—*Exp. Eye Res.,* 67:341–346 (1998).

Kaunitz, J., et al., "Effect of Orogastric Nicotine on Rat Gastric Mucosal Gel Thickness, Surface, Cell Viability and Intracellular pH1,"—*J. Pharmacol. Exp. Ther.,* 265:948–954 (1993).

Kessler, T and Darlene A. Dartt, "Neural Stimulation of Conjnctival Goblet Mucous Secretion in Rats,"—*Adv. Exp. Med. Biol.* 350:393–398 (1994).

Kuo, Han–Pin, et al., "Cigarette smoke–induced airway goblet cell secretion: dose–dependent differential nerve activation,"—*Am. J. Physiol.* 263:L161–167 (1992).

Lang, M., et al., "Effect of Systemic Nicotine on Mucus Secretion from Tracheal Submucosal Glands and on Cardiovascular, Pulmonary, and Hematologic Variables,"—*Klin. Wochenschr.* 66:170–179 (1988).

Latli, B., et al., "Novel and Potent 6–Chloro–3–pyridinyl Ligands for the 4 2 Neuronal Nicotinic Acetylcholine Receptor,"—*J. Med. Chem.* 42:2227–2234 (1999).

Leino, M and Arto Urtti., p. 245–264, in Ocular Therapeutics and Drug Delivery, A multidisciplinary Approach, Ed. I.K. Reddy, Technomic Publishing, Lancaster, PA (1996).

Lemp, M., "Is the Dry Eye Contact Lenms Wearer at Risk?,"—Corena 9:S48–550 (1990).

Matsushima, D., et al., "Absorption and Adverse Effects following Topical and Oral Administration of Three Transdermal Nicotine Products to Dogs,"—*J. Pharm. Sci.,* 84:365–369 (1995).

Morris, G., et al., "Gastric Cytoprotection Is Secondary to Increased Mucosal Fluid Secretion: A study of Six Cytoprotective Agents in the Rat,"—*J. Clin Gastroenterol,* 27:S53–63 (1998).

Nakamura, M., et al., "Gefarnate Stimulates Secretion of Mucin–Like Glycoproteins by Corneal Epithelium in Vitro and Protects Corneal Epithelium from Dessication in Vivo, "—*Exp. Eye Res.,* 65:569–574 (1997).

Novack, G., "Ocular Toxicology,"—*Curr. Opin. Ophthalmol.,* 5:110–114 (1994).

Pullen, R., "Colonic mucus, smoking and ulcerative colitis, "—*Ann. R. Coll. Engl.* 78:85–91 (1996).

Richardson, P.A., et al., "The control of airway mucus secretion,"—*Eur. J. Respir. Dis. Suppl.* 153:43–51 (1987).

Rolando, M., et al., "Ocular Surface changes induced by repeated Impression Cytology,"—*Adv. Exp. Med. Bio.* 350:249–254 (1994).

Sopori, M., "Immunosuppressive and Anti–Inflammatory Properties of Nicotine,"—Neuronal Nicotine Receptors: Pharmacology and Therapeutic Oppostunities, Edit. By A.P. Arneic and J.D. Brioni, pp. 197–209.

Stern, M., et al, "A Unified Theory of the Role of the Ocular Surface in Dry Eye,"—*Adv. Exp. Med. Biol.,* 438:643–651 (1998).

Vernier, J., et al., "4–[1–Methyl–2–pyrrolidinyl)ethl]thio] –phenol Hydrochloride (SIB–1553A): A Selectivity for Neuronal Nicotinic Acetylcholine Receptors,"—*J. Med. Chem.* 42:1684–1686 (1999).

Villemagne, V., et al., "Nicotine and Related Compounds as PET and SPECT Ligands,"—Neuronal Nicotinic Receptors, Eds. Arneric and Brioni, Weley–Liss, Inc. p.235–250 (1999).

Wakakura, M., et al., "Rapid increase in Cytosolic calcium ion concentration mediated by acetylcholine receptors in cultured rentinal neurons and Muller cells,"—*Arch. Clin. Exp. Ophthalmol.,* 236:934–939 (1998).

Wanner, A., et al., "Mucociliary Claerance in the Airways, "—*Am. J. Respir. Crit. Care Med.,* 154:1868–1902 (1996).

Zijlstra, F J., et al., "Effect of nicotine on rectal mucus and mucosal eicosanoids,"—*Gut,* 35:247–251 (1994).

* cited by examiner

METHOD OF TREATING DRY EYE DISEASE WITH NICOTINIC ACETYLCHOLINE RECEPTOR AGONISTS

TECHNICAL FIELD

This invention relates to a method of treating dry eye disease and corneal injury by administering to a patient a nicotinic acetylcholine receptor agonist such as nicotine, epibatidine alkaloids and their analogs thereof.

BACKGROUND OF THE INVENTION

There are many situations where it is therapeutically desirable to increase the amount of tear fluid produced by the eye. Dry eye disease is the general term for indications produced by abnormalities of the precorneal tear film characterized by a decrease in tear production or an increase in tear film evaporation, together with the ocular surface disease that results. Approximately 38 million Americans are affected with some type of dry eye disorder. Dry eye disease includes keratoconjunctivitis sicca (KCS), age-related dry eye, Stevens-Johnson syndrome, Sjogren's syndrome, ocular cicatrical pemphigoid, blepharitis, Riley-Day syndrome, and congenital alacrima. Dry eye disease can also be caused by nutritional disorders or deficiencies (including vitamins), pharmacologic side effects, eye stress and glandular and tissue destruction, environmental exposure to smog, smoke, excessively dry air, airborne particulates, autoimmune and other immunodeficient disorders, and comatose patients who are unable to blink.

Corneal transparency is essential for the maintenance of visual function and is contingent on the flawless integrity of all its components: the epithelium, stroma, and endothelium. Disruption of the epithelial anatomic barrier activates healing and remodeling processes, which can predispose the tissue to stromal ulceration and/or cause stromal opacification, ultimately leading to irreversible visual deficit. Corneal injury is caused by any insult to the ocular surface: infection, trauma, chemical burns, contact lens wear, topical drug abuse, and postoperative damage. Dry eye can also cause corneal injury. Despite the numerous studies published in recent years that have indicated that cytokines, growth factors, and neuorpeptides can influence the epithelial proliferations and differentiations in vitro, a precise therapeutic approach to modulate the healing process has not yet been defined.

A healthy precorneal tear film has several important functions: 1) to protect the cornea from desiccation; 2) to aid in the immune response to infections; 3) to enhance oxygen permeation into the cornea; 4) to allow gliding movement of the eyeball and eyelids; and 5) to help maintain the ocular pressure through osmosis. There are two structures responsible for maintaining the properties of the tear film—the lacrimal glands and the conjunctiva (the mucous membrane which surrounds part of the eyeball and inner eyelids). These structures maintain the tear film via regulation of water and electrolyte transport and via mucin release by goblet cells.

The progression of dry eye disease is characterized by four main steps. The first step is a decrease in tear production. In rabbit models, this decrease in tear production has been shown to correlate with an increase in tear osmolarity. The second step is a loss of mucous-containing conjunctival goblet cells. This decrease in goblet cell density becomes evident several weeks after the onset of decreased tear production. The third step in the progression of dry eye disease occurs about 1 year later when desquamation of the corneal epithelium is observed. The fourth and last step of the disease is a destabilization of the cornea-tear interface (Gilbard, CLAO Journal 22:141–45 (1996)).

Currently, the pharmaceutical treatment of dry eye disease is mostly limited to administration of artificial tears (saline solution) to temporarily rehydrate the eyes. However, relief is short-lived and frequent dosing is necessary. In addition, artificial tears often have contra-indications and incompatibility with soft contact lenses (Lemp, Cornea 9: S48–550 (1990)). The use of phosphodiesterase inhibitors, such as 3-isobutyl-1-methylxanthine (IBMX) to stimulate tear secretion is disclosed in U.S. Pat. No. 4,753,945. The effectiveness of these phosphodiesterase inhibitors is currently being investigated (Gilbard, et al., Arch. Ophthal, 109:672–76 (1991) and 112:1614–16 (1994); idem, Inv. Ophthal. Vis. Sci. 31:1381–88 (1990)). Stimulation of tear secretion by topical application of melanocyte stimulating hormones is described in U.S. Pat. No. 4,868,154.

In addition, a topical ophthalmic formulation of cyclosporine (Restasis) has been investigated as a treatment of immune-based dry eye disease (Stern et al., Adv. Exp. Med. Biol., 438:643–651 (1998)). Stimulation of ocular mucin secretion has also been demonstrated with hydroxyeicosatetraenoic acid derivatives (Yanni, et al., U.S. Pat. No. 5,696, 166), gefarnate (Nakamura et al., Exp. Eye Res., 65:569–574 (1997)). U.S. Pat. No. 5,900,407 and WO 98/34593 (Yerxa et al.) disclose a method of stimulating tear secretion from lacrimal tissue by administering to the eyes an effective amount of purinergic receptor agonists such as uridine 5'-triphosphate, cytidine 5'-triphosphate, adenosine 5'-triphosphate, dinucleotides, and their analogs. Jumblatt and Jumblatt (Exp. Eye Res., 67:341–346 (1998)) demonstrate the effects of adenine analogues on secretion of high molecular weight, mucin-like glycoprotein by conjunctival goblet cells.

Mucus is a viscous, lubricating material that recruits and maintains moisture to the surfaces it coats. Mucus is actively secreted with salt and water onto surfaces that require these hydrating and lubricating properties for normal functioning (Forstner et al., Adv. Exp. Med. Biol. 144:199–224 (1982)). Mucus is particularly important in the normal functioning of the ocular surface.

Goblet cells are the primary cell type responsible for secreting gel-forming mucins in epithelial tissues; they secrete mucin in response to neural stimulation. In the eye for example, mechanical stimulus of the cornea causes goblet cell mucin secretion, presumably via neurotransmitter release (Kessler, et al., Adv. Exp. med. Biol. 350:393–8 (1994)). It is known that $P2Y_2$ receptor agonists, such as ATP, cause mucin secretion and that mechanical stimulus of the cornea triggers local ATP release (Jensen et al, poster presentation at American Academy of Optometry annual meeting, December, 1999, Seattle, Wash.). In addition, neurotransmitters, such as epinephrine, phenylephrine, serotonin, dopamine and vasoactive intestinal peptide (VIP), cause mucin secretion when topically applied to the eye.

Secretion from lacrimal glands, is under neural control of the parasympathetic and sympathetic efferent nerves that innervate the secretory acinar cells of the glands. These nerves contain the parasympathetic neurotransmitters acetylcholine and vasoactive intestinal peptide, which are believed to stimulate secretion of salt, water and protein via activation of muscarinic receptors that increase intracellular calcium concentration in the acinar cells (Dartt, p.1 –9, in Lacrimal Gland, Tear Film, and Dry Eye Syndromes, Ed. Sullivan, Plenum Press, New York, (1994)).

Muscarinic acetylcholine receptor agonists have thus been targeted towards Sjogren's syndrome related dry eye and dry mouth. Pilocarpine, a non-selective muscarinic agonist, is used systemically for dry eye and dry mouth under the trade name Salagen®. The topical ophthalmic formulation of pilocarpine is not useful for dry eye because it causes spasm of accommodation. This miotic, neuromotor effect is useful instead for lowering intraocular pressure in glaucoma patients (Leino and Urtti, P. 245–247, in Ocular Therapeutics and Drug Delivery, A Multidisciplinary Approach, Ed. I. K. Reddy, Technomic Publishing, Lancaster, Pa. (1996)).

Nicotinic acetylcholine receptors (nAChRs), present in a variety of tissues, are heterologous receptors made up of several subunits. Various nAChR subtypes exist and they show a complex regulation of calcium concentration and mediation of neurotransmitter (e.g. dopamine) release.

Nicotinic agonists have many pharmacological actions when applied locally or systemically, and synthetic compounds are being targeted towards a number of therapeutic indications including: Alzheimer's disease, Parkinson's disease, smoking cessation, epilepsy, neuroprotection, attention deficit disorder and pain (*Neuronal Nicotinic Receptors: Pharmacology and Therapeutic Opportunities*, Eds. Arneric and Brioni, Wiley-Liss, Inc. (1999)). Nicotinic agonists, such as nicotine, stimulate the secretion of mucus when applied to the mucosal surfaces of the lung and stomach, and is believed to have protective effects on ulcerative colitis presumably by increasing colonic mucin secretion (Morris, et al., *J Clin Gastroenterol*, 27: S53–63 (1998), Finnie, et al., *Clin. Sci.*, 91:359–364 (1996), Zijlstra, et al., *Gut*, 35:247–251 (1994); Kaunitz, et al., *J Pharmacol. Exp. Ther.*, 265:948–954 (1993)). Transdermal nicotine has been used clinically as therapy for ulcerative colitis (Pullen, *Ann. R. Coll. Surg. Engl.* 78:85–91 (1996)).

The nicotine-associated effects of cigarette smoking have been studied extensively and it is well established that tobacco smoking leads to chronic bronchitis and mucus hypersecretion (Coles, et al., *Am. J Pathology*, 94:459–471 (1979); Wanner, et al., *Am. J Respir. Crit. Care Med.*, 154:1868–1902, (1996). "Topical" tobacco smoke causes mucin secretion from airway goblet cells and systemic nicotine causes increased tracheal mucus secretion (Kuo, et al., *Am. J Physiol.* 263: L161–167 (1992); Lang, et al.; *Klin. Wochenschr.* 66:170–179 (1988); Hummer, et al., *Klin. Wochenschr.* 66:161–169 (1988), Richardson, et al., *Eur. J Respir. Dis. Suppl.* 153:43–51 (1987)). These pro-secretory effects of nicotine have been largely thought of as deleterious, with the exception of the association of less frequent ulcerative colitis among cigarette smokers.

Recent advances in the field of nicotine receptors has revealed that it is possible to create ligands for specific nicotinic receptor subtypes, thereby reducing or eliminating altogether the unwanted side effects of nicotine, such as neuromotor and cardiovascular effects (Brioni et al., *Behav. Neural. Biol.* 59:57–62 (1993); Brioni, et al., *Adv. Pharmacol.* 37:153–214 (1997)) The field of therapeutic nicotinic agonists largely focuses on the central nervous system effects of nicotinic agonists and their ability to stimulate cognition (U.S. Pat. Nos. 5,922,723 and 5,861,423). The mild antiinflammatory effects of nicotine are established; smokers have been shown to have a lower incidence of inflammatory diseases such as ulcerative colitis, sarcoidosis, pigeon breeder's disease, fanner's lung, allergies, endometriosis, uterine fibroids and acne (Amie & Grioni Ch. 11, p. 205). Nicotine has also been investigated for its effects on CNS inflammation (Brioni, et al., (1997), supra) based diseases.

It is known that nicotine from tobacco smoke lowers ocular blood flow (Novack, *Curr. Opin. Ophthalmol.*, 5:110–4 (1994)) and that nicotinic receptors are located in the retina (Wakakura, et al., *Arch. Clin. Exp. Ophthalmol.*, 236:934–9, (1998); Baldridge, *J Neurosci.*, 16:5060–72, (1996)), but the effects of nicotinic agonists on ocular surface hydration and lubrication is unknown. Nicotine has been added to the ocular and oral mucosal surfaces to evaluate effects on sensory neuron-mediated irritation responses (Carstens, et al., *J Neurophysiol.*, 80:465–92 (1998)).

Because of the ability of nicotinic agonists to stimulate secretion in the lung and gastrointestinal tract, Applicants were motivated to investigate whether nicotinic agonists could effect hydration and lubrication of the ocular surface, and thus be effective in treating dry eye diseases and disorders of impaired hydration and lubrication. Applicants have found that nicotinic receptor agonists, when given topically or systemically, provide a therapeutic effect of treating dry eye disease by increasing the hydration and lubricating properties and reducing inflammation of ocular surfaces. The present invention may also be useful as a wash or irrigation solution in conscious individuals, during surgery for treating corneal wounds, or to maintain comatose patients or those who cannot blink due to neuromuscular blockade or loss of the eyelids.

SUMMARY OF THE INVENTION

The invention provides a method of increasing hydration and lubrication of ocular surfaces. The method comprises administering to a patient a pharmaceutical composition comprising a nicotinic acetylcholine receptor agonist in an amount effective to increase hydration and lubrication in the eyes.

The pharmaceutical composition used in this invention comprises a nicotinic receptor agonist together with a pharmaceutically acceptable carrier thereof. Nicotinic receptor agonists include but are not limited to: nicotine and its analogs, trans-metanicotine and its analogs, epibatidine and its analogs, pyridol derivatives, piperidine alkaloids such as lobeline and its analogs, certain para-alkylthiophenol derivatives, and imidacloprid and its analogs.

The compounds of the present invention are potent agonists of nicotinic receptors; thus, they are useful in the treatment of diseases in which hydration and lubrication is impaired, such as dry eye disease, corneal injury and Sjogren's syndrome.

DETAILED DESCRIPTION OF THE INVENTION

The invention provides methods for treating dry eye diseases and corneal injury using a nictonic receptor agonist. The method comprises topically or systemically administering to a subject in need thereof a pharmaceutical composition comprising a nicotinic receptor agonist in an amount effective to stimulate conjunctival goblet cells to secrete mucin, thereby increasing hydration and lubrication in the eyes. The nicotinic receptor agonist stimulates nicotinic acetylcholine receptors, which leads to prosecretory effects, either directly via neural stimulation or indirectly through stimulation of dopamine release.

The pharmaceutical compositions useful in this invention comprise a nicotinic acetylcholine receptor agonist (Formula I–X) together with a pharmaceutically acceptable carrier therefor. Useful compositions also include a nicotinic receptor agonist bound to a polymer such as polyethyleneglycol, such compositions are not absorbed systemically. Various nicotine cholinergic receptor agonists are described in Benowitz, et al., P 213–234; Villemagne, et al., p. 235–250; and Holladay, et al., P. 253–270 in *Neuronal Nicotinic Receptors*, Eds. Arneric and Brioni, Wiley-Liss, Inc. (1999); Vernier, et al., *J. Med. Chem.* 42: 1684–1686 (1999), and Latli, et al., *J Med. Chem.* 42: 2227–2234 (1999). Nicotinic receptor agonists include but are not limited to: nicotine and its analogs, trans-metanicotine and its analogs, epibatidine and its analogs, pyridol derivatives, piperidine alkaloids such as lobeline and its analogs, and certain paraalkylthiophenols.

Nicotine and its analogs are depicted by general formula I:

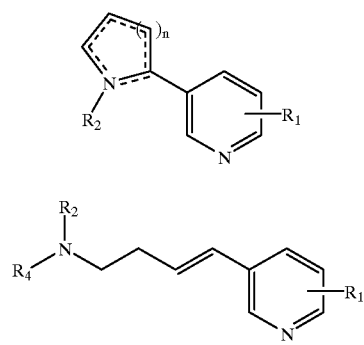

Formula I

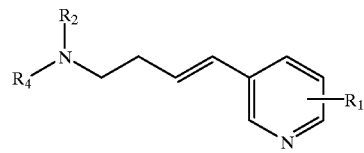

Formula II

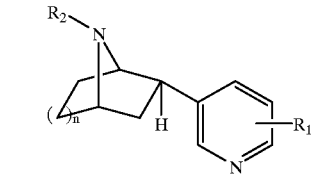

Formula III

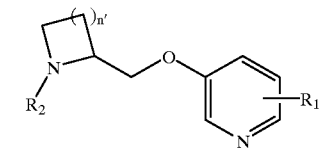

Formula IV

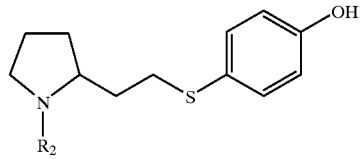

Formula V

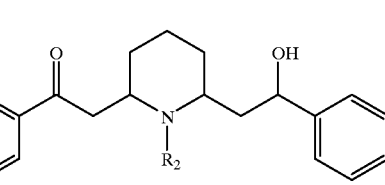

Formula VI

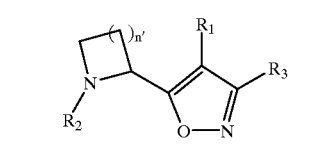

Formula VII

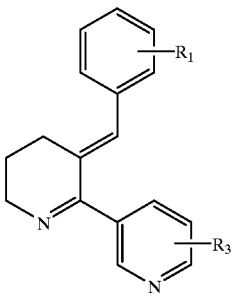

Formula VIII

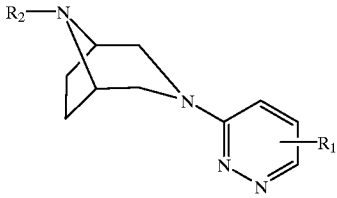

Formula IX

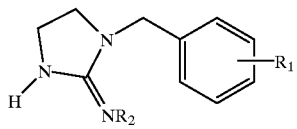

Formula X wherein:
n is an integer between 0–3;
n' is an integer between 1–3;
$R_1$, and $R_3$ are H, $C_1$–$C_6$ alkyl, $C_2$–$C_6$ alkenyl, $C_2$–$C_6$ alkynyl, $C_3$–$C_7$ cycloalkyl, $C_4$–$C_7$ cycloalkenyl, $C_1$–$C_6$ alkoxy, Cl, Br, I, or amino; wherein at least one hydrogen of said alkyl, alkenyl, alkynyl, cycloalkyl, cycloalkenyl, $C_1$–$C_6$ alkoxy, is optionally substituted with a moiety selected from the group consisting of halogen, hydroxy, carboxy, cyano, nitro, sulfonamido, sulfonate, phosphate, sulfonic acid, amino, $C_{14}$ alkylamino, and di-$C_{14}$ alkylamino, wherein said alkyl groups are optionally linked to form a heterocycle; and
$R_2$ and $R_4$ are H, $C_1$–$C_6$ alkyl, $C_2$–$C_6$ alkenyl, $C_2$–$C_6$ alkynyl, $C_3$–$C_7$ cycloalkyl, $C_4$–$C_7$ cycloalkenyl, $C_1$–$C_6$ alkoxy, or amino; wherein at least one hydrogen of said alkyl, alkenyl, alkynyl, cycloalkyl, cycloalkenyl, $C_1$–$C_6$ alkoxy, is optionally substituted with a moiety selected from the group consisting of halogen, hydroxy, carboxy, cyano, nitro, sulfonamido, sulfonate, phosphate, sulfonic acid, amino, $C_{1-4}$ alkylamino, and di-$C_{1-4}$ alkylamino, wherein said alkyl groups are optionally linked to form a heterocycle; optionally $R_2$ and $R_4$ in Formula II are linked to form a 5 or 6-membered ring.

The stereochemistry of compounds of Formulae I to X useful in this invention can be either levoratatory (S)-isomer, (R)-isomer, or a mixture of R/S isomers (racemic).

Nicotine analogs of Formula I useful in this invention include nicotine, 5-ethynylnicotine, nornicotine, cotinine, nicotyrine, nicotine-N'-oxide, anabasine, anatabine, myosmine, β-nomicotyrine, N'-methylanabasine, N'-methylanatabine, N'-methylmyosmine, and 2, 3'-bipyridyl. Preferred compounds, for example, are: (−)-nicotine, anabasine, and 5-ethynylnicotine.

Preferred compounds of Formula II include trans-metanicotine and 3-ethoxy-trans-metanicotine (without N-methyl group).

Preferred epibatidine analogs of Formula III include epibatidine and its derivatives wherein the chlorine (Cl) on the pyridine ring is replaced by F, Br, I, H, or methyl.

Preferred compounds of Formula IV include [2-methyl-3-(2-(S)-pyrrolidinylmethoxy) pyridine dihydrochloride], ABT-089 (n=2, $R_1$=1-methyl and $R_2$=H); -(2-azetidinylmethoxy)-2-chloropyridine, ABT-594 (n=1,$R_1$=2-chloro and $R_2$=H).

Preferred compounds of Formula V include thioalkylphenol derivatives with $R_1$=methyl, trifluoromethyl, or ethyl. An example of a preferred compound is 4-[[2-(1-methyl-2-pyrrolidinyl)ethyl]thio]phenol hydrochloride (SIB- 1553A) Preferred compounds of Formula VI are lobeline analogs with $R_1$=$CH_3$ (lobeline) or $R_1$=ethyl.

Preferred compounds of Formula VII include (S)-3-methyl-5-(1-methyl-2-pyrolidinyl) isoxazole hydrochloride, ABT-418 (n=2, $R_1$=3-methyl and $R_2$=$CH_3$); and n=2, $R_1$=ethynyl, $R_2$=$CH_3$.

Preferred compounds of Formula VIII include $R_1$=2,4-dimethoxy (known as DMXB); $R_1$=2,4-diethoxy; or $R_1$=2, 4-dichloro.

Preferred compounds of Formula IX include $R_1$=6-chloro and $R_2$=H (DBO-083); and $R_1$=6-chloro and $R_2$=methyl.

Preferred compounds of Formula X include imidacloprid ($R_1$=Cl, $R_2$=$NO_2$), desnitro-imidacloprid ($R_1$=Cl, $R_2$=H).

Some compounds of Formulas I—X can be made by methods known to those skilled in the art; some compounds are commercially available, for example from Sigma Chemical Co. (St. Louis, Mo.). Compounds of Formula I and VIII can be made in accordance with known procedures described by Kem et al (U.S. Pat. No. 5,741,802) and McDonald et al (U.S. Pat. No. 5,723,477). Compounds of Formula II can be made in accordance with known procedures described by Caldwell et al (U.S. Pat. No. 5,861,423). Compounds of Formula III can be made in accordance with known procedures described by Bencherif et al (U.S. Pat. No. 5,922,723), Shen et al (U.S. Pat. No. 5,817,679), and Badio et al. (*Eur. J. Pharmacol.* 321:189–194 (1997)). Compounds of Formula IV can be made in accordance with known procedures described by Nan-Horng et al (WO/9746554A1). Compounds of Formula V can be made in accordance with known procedures described by Vernier et al., *J. Med. Chem.* 42:1684–6 (1999). Compounds of Formula VI can be made in accordance with known procedures described by Crooks et al (U.S. Pat. No. 5,830,904). Compounds of Formula VII can be made in accordance with known procedures described by Garvey, et al. *J. Med. Chem.* 37:4455–63 (1994). Formula X can be made in accordance with known procedures described by Latli et al., *J. Med. Chem.* 42:2227–34 (1999).

The active compounds of the invention may also be present in the form of their pharmaceutically acceptable salts, such as, but not limited to, an acid salt such as acetates, tartrates, chloride, phosphate, sulfates, sulfites, carbonates, bicarbonate and citrates. Pharmaceutically acceptable salts are salts that retain the desired biological activity of the parent compound and do not impart undesired toxicological effects.

The active compounds disclosed herein may be administered topically or systemically. For topical application, the active compounds are administered to the eyes of a patient by any suitable means, but are preferably administered by a liquid or gel suspension of the active compound in the form of drops, spray or gel. Alternatively, the active compounds may be applied to the eye via liposomes. Further, the active compounds may be infused into the tear film via a pump-catheter system. Another embodiment of the present invention involves the active compound contained within a continuous or selective-release device, for example, membranes such as, but not limited to, those employed in the Ocusert™ System (Alza Corp., Palo Alto, Calif.). As an additional embodiment, the active compounds can be contained within, carried by, or attached to contact lenses which are placed on the eye. Another embodiment of the present invention involves the active compound contained within a swab or sponge which can be applied to the ocular surface. Another embodiment of the present invention involves the active compound contained within a liquid spray which can be applied to the ocular surface.

The topical solution containing the active compound may contain a physiologically compatible vehicle, as those skilled in the ophthalmic art can select, using conventional criteria. The vehicles may be selected from the known ophthalmic vehicles which include, but are not limited to, saline solution, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

In addition to the topical method of administration described above, various methods can be used to administer the active compounds of the present invention systemically to eyes. The term systemic as used herein includes subcutaneous injection; intravenous, intramuscular, intrasternal injection; infusion; inhalation, transdermal administration, oral administration; and intra-operative instillation.

One systemic method involves an aerosol suspension of respirable particles comprising the active compound, which the subject inhales. The active compound would be absorbed into the bloodstream via the lungs, and subsequently contact the lacrimal glands in a pharmaceutically effective amount. The respirable particles may be liquid or solid, with a particle size sufficiently small to pass through the mouth and larynx upon inhalation; in general, particles ranging from about 1 to 10 microns, but more preferably 1–5 microns, in size are considered respirable.

Another method of systemically administering the active compounds to the eyes of the subject would involve administering a liquid/liquid suspension in the form of eye drops or eye wash or nasal drops of a liquid formulation, or a nasal spray of respirable particles which the subject inhales. Liquid pharmaceutical compositions of the active compound for producing a nasal spray or nasal or eye drops may be prepared by combining the active compound with a suitable vehicle, such as sterile pyrogen free water or sterile saline by techniques known to those skilled in the art.

The active compounds may also be systemically administered to eyes through absorption by the skin using transdermal patches or pads. Suitable transdermal systems include: Nicoderm, with a drug reservoir and a rate-controlling membrane; Nicotinell, with a nicotine solution dispersed in a cotton gauze pad between layers of adhesive; and Niconil, with a nicotine gel matrix. (Matsushima et al., *J. Pharm. Sci.*, 84:365–369 (1995)). The active compounds are absorbed into the bloodstream through the skin. Plasma concentration of the active compounds can be controlled by using patches containing different concentrations of active compounds.

Other methods of systemic administration of the active compound involves oral administration, in which pharmaceutical compositions containing compounds of Formulae I–X are in the form of tablets, lozenges, aqueous or oily suspensions, viscous gels, chewable gums, dispersible powders or granules, emulsion, hard or soft capsules, or syrups or elixirs. Tablets contain the active ingredient in admixture with nontoxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Formulation for oral use may also be presented as chewable gums by embedding the active ingredient in gums so that the active ingredient is slowly released upon chewing.

Additional means of systemic administration of the active compound to the eyes of the subject would involve a suppository form of the active compound, such that a therapeutically effective amount of the compound reaches the eyes via systemic absorption and circulation.

Further means of systemic administration of the active compound involve direct intra-operative instillation of a gel, cream, or liquid suspension form of a therapeutically effective amount of the active compound.

For systemic administration such as injection and infusion, the pharmaceutical formulation is prepared in a sterile medium. The active ingredient, depending on the vehicle and concentration used, can either be suspended or dissolved in the vehicle. Adjuvants such as local anaesthetics, preservatives and buffering agents can also be dissolved in the vehicle. The sterile injectable preparation may be a sterile injectable solution or suspension in a non-toxic acceptable diluent or solvent. Among the acceptable vehicles and solvents that may be employed are sterile water, saline solution, or Ringer's solution.

For oral use, an aqueous suspension is prepared by addition of water to dispersible powders and granules with a dispersing or wetting agent, suspending agent one or more preservatives, and other excipients. Suspending agents include, for example, sodium carboxymethylcellulose, methylcellulose and sodium alginate. Dispersing or wetting agents include naturally-occurring phosphatides, condensation products of an allylene oxide with fatty acids, condensation products of ethylene oxide with long chain aliphatic alcohols, condensation products of ethylene oxide with partial esters from fatty acids and a hexitol, and condensation products of ethylene oxide with partial esters derived from fatty acids and hexitol anydrides. Preservatives include, for example, ethyl, and n-propyl p-hydroxybenzoate. Other excipients include sweetening agents (e.g., sucrose, saccharin), flavoring agents and coloring agents. Those skilled in the art will recognize the many specific excipients and wetting agents encompassed by the general description above.

For rectal administration, the compositions in the form of suppositories can be prepared by mixing the active ingredient with a suitable non-irritating excipient which is solid at ordinary temperatures but liquid at the rectal temperature and will therefore melt in the rectum to release the compound. Such excipients include cocoa butter and polyethylene glycols.

Plasma concentrations of active compounds delivered by any means may vary according to compounds, but are generally 0.1–100 ng/mL; preferably, 0.5–50 ng/mL; and more preferably, 5–25 ng/mL. Topical or local doses vary based on site of delivery, but are generally 0.001–10 mg; preferably, 0.01–5 mg; and, more preferably, 0.05–0.5 mg.

The invention is illustrated further by the following examples of treatment which are not to be construed as limiting the scope or spirit to the specific procedures described in them. In vivo examples in accordance with the invention are conducted on rabbits with dry eye disease. The dry eye disorder is created by surgically closing the duct that carries fluid from the main lacrimal gland to the tear film and surgically removing the nictitans and harderian glands. It is recognized by those skilled in the art that results of ophthalmologic tests carried out on the aforementioned rabbit model have close correlation with humans afflicted with dry eye disease, and, therefore, the results provide an accurate prediction of therapeutic efficacy in humans.

EXAMPLES

Example 1

Effects of a Topical Nicotinic Agonist in a Rabbit Model of Dry Eye Disease Dry eye is created in rabbits by surgically removing the lacrimal glands and allowing the signs and symptoms of dry eye to develop for at least 4 weeks (Gilbard, *CLAO J.*, 22:141–145 (1996)). After confirming signs of dry eye by the Schirmer test and ocular surface staining, trans-metanicotine (as a neutral, buffered tartrate salt) at concentrations of either 0.01, 0.1 and 1.0% is instilled as a 50 microliter drop to the ocular surface up to 5 times a day, every day for 4 weeks. The signs of dry eye are monitored once a week for 4 weeks and an increase in Schirmer scores and/or a decrease in the amount of ocular surface staining indicates the efficacy of the nicotinic agonist in the treatment of dry eye disease.

Example 2

Treatment of Systemic Dryness with a Nicotinic Agonist

A Sjogren's syndrome patient with signs and symptoms of ocular, dryness is treated with an oral or transdermal dosage form of a compound of Formulae I–X such that the plasma levels of the agonist are between 5–25 ng/mL. The dosage level is maintained on a daily basis by one to three times a day of oral dosing or one to three patches over 24–60 hours of transdermal dosing. After 2–8 weeks of dosing the signs and symptoms of systemic dryness are alleviated by the nicotinic agonist.

Example 3

Stimulation of Mucin Release from Mucosal Goblet Cells

The following is an example of a method for measuring the effects of a nicotinic receptor agonist in vivo on mucin secretion from mucous membranes using impression cytology. Impression cytology is a technique used to stain and identify mucin-containing goblet cells (Rolando, M., et al., *Adv. Exp. Med. Bio.* 350:249 (1994)).

A compound of Formula I–X or a saline solution is applied to the mucosal surface and impression cytology is performed 5,15, 30 and 60 minutes after application of solution. The specimens are stained with periodic acid and Schiff s reagent (AB-PAS), and the area of PAS staining is analyzed by compouter software (Winroof or BioQuant). A decrease in the area of AB-PAS staining compared to saline control indicates that the compound stimulates mucin secretion from goblet cells of mucus membranes.

The invention and the manner and process of making and using it are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A method of treating dry eye disease comprising administering to a subject in need of such treatment a therapeutically effective amount of a nicotinic acetylcholine receptor agonist in a pharmaceutically effective carrier.

2. The method according to claim 1, wherein said nicotinic acetylcholine receptor agonist is selected from the group consisting of compounds of Formula I–X:

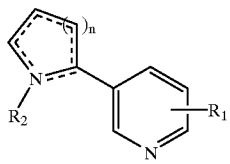

Formula I

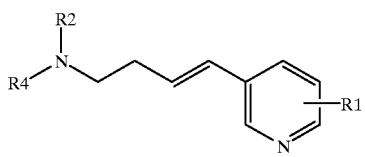

Formula II

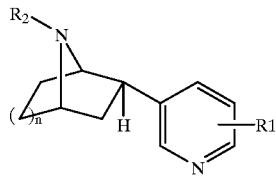

Formula III

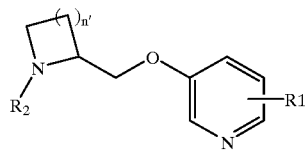

Formula IV

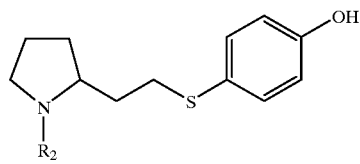

Formula V

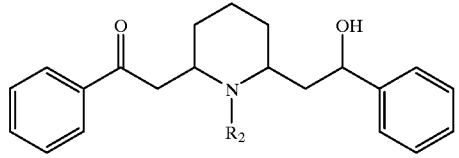

Formula VI

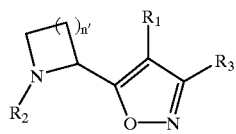

Formula VII

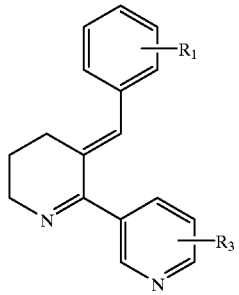

Formula VIII

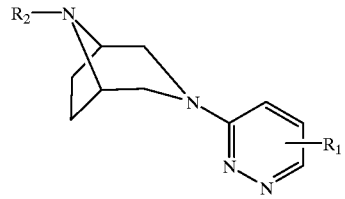

Formula IX

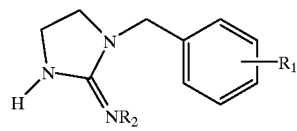

Formula X wherein:

n is an integer between 0–3;

n' is an integer between 1–3;

$R_1$, and $R_3$ are H, $C_1$–$C_6$ alkyl, $C_2$–$C_6$ alkenyl, $C_2$–$C_6$ alkynyl, $C_3$–$C_7$ cycloalkyl, $C_4$–$C_7$ cycloalkenyl, $C_1$–$C_6$ alkoxy, Cl, Br, I, or amino; wherein at least one hydrogen of said alkyl, alkenyl, alkynyl, cycloalkyl, cycloalkenyl, $C_1$–$C_6$ alkoxy, is optionally substituted with a moiety selected from the group consisting of halogen, hydroxy, carboxy, cyano, nitro, sulfonamido, sulfonate, phosphate, sulfonic acid, amino, $C_{1-4}$ alkylamino, and di-$C_{1-4}$ alkylamino, wherein said alkyl groups are optionally linked to form a heterocycle; and $R_2$ and $R_4$ are H, $C_1$–$C_6$ alkyl, $C_2$–$C_6$ alkenyl, $C_2$–$C_6$ alkynyl, $C_3$–$C_7$ cycloalky, $C_4$–$C_7$ cycloalkenyl, $C_1$–$C_6$ alkoxy, or amino; wherein at least one hydrogen of said alkyl, alkenyl, alkynyl, cycloalkyl, cycloalkenyl, $C_1$–$C_6$ alkoxy, is optionally substituted with a moiety selected from the group consisting of halogen, hydroxy, carboxy, cyano, nitro, sulfonamido, sulfonate, phosphate, sulfonic acid, amino, $C_{1-4}$ alkylamino, and di-$C_{1-4}$ alkylamino, wherein said alkyl groups are optionally linked to form a heterocycle; optionally $R_2$ and $R_4$ in Formula II are linked to form a 5 or 6-membered ring.

3. A method according to claim 2, wherein said nicotinic acetylcholine receptor agonist is nictotine and its analogs.

4. A method according to claim 2, wherein said nicotinic acetylcholine receptor agonist is trans-metanicotine and its analogs.

5. A method according to claim 2, wherein said nicotinic acetylcholine receptor agonist is a pyridol derivative.

6. A method according to claim 2, wherein said nicotinic acetylcholine receptor agonist is a piperidine alkaloid.

7. A method according to claim 2, wherein said nicotinic acetylcholine receptor agonist is a para-alkylthiophenol derivative.

8. The method according to claim 1, wherein said administering involves topical administration of said compound.

9. The method according to claim 8, wherein said topical administration is via a carrier vehicle selected from a group consisting of drops of liquid, liquid washes, gels, ointments, sprays and liposomes.

10. The method according to claim 8, wherein said topical administration comprises infusion of said compound to said ocular surface via a device selected from a group consisting of a pump-catheter system, a continuous or selective release device and a contact lens.

11. The method according to claim 1, wherein said administering is systemic administration of said compound.

12. The method according to claim 11, wherein said systemic administration involves administration of a liquid/liquid suspension of said compound via nose drops or nasal spray, or administration of a nebulized liquid to oral or nasopharyngeal airways of said subject, such that a therapeutically effective amount of said compound contacts lacrimal tissues of said subject via systemic absorption and circulation.

13. The method according to claim 11, wherein said systemic administration of said compound is accomplished by administering an oral form of said compound, such that a therapeutically effective amount of said compound contacts lacrimal tissues of said subject via systemic absorption and circulation.

14. The method according to claim 13, wherein said oral form is a chewable gum.

15. The method according to claim 11, wherein said systemic administration involves administration of an injectable form of said compound, such that a therapeutically effective amount of said compound contacts lacrimal tissues of said subject via systemic absorption and circulation.

16. The method according to claim 11, wherein said systemic administration involves administration of a suppository form of said compound, such that a therapeutically effective amount of said compound contacts lacrimal tissues of said subject via systemic absorption and circulation.

17. The method according to claim 11, wherein said systemic administration involves administration of an intra-operative instillation of a gel, cream, powder, foam, crystals, liposomes, spray or liquid suspension form of said compound, such that a therapeutically effective amount of said compound contacts the lacrimal tissues of said subject via systemic absorption and circulation.

18. The method according to claim 11, wherein said systemic administration involves administration of said compound in a form of a transdermal patch or a transdermal pad, such that a therapeutically effective amount of said compound contacts the lacrimal tissues of said subject via systemic absorption and circulation.

19. A method of increasing hydration and lubrication of ocular surfaces comprising the steps of administering to a subject an amount of a nicotinic acetylcholine receptor agonist effective to stimulate conjunctival goblet cells to secrete mucins.

20. The method according to claim 19, wherein said nicotinic acetylcholine receptor agonist is selected from the group consisting of compounds of Formula I–X as described in claim 2.

21. A method of treating corneal injury comprising administering to a subject in need of such treatment a pharmaceutical formulation comprising a therapeutically effective amount of a nicotinic acetylcholine receptor agonist selected from the group consisting of compounds of Formulae I–X as described in claim 2.

* * * * *